US011109947B2

(12) United States Patent
Adamson et al.

(10) Patent No.: US 11,109,947 B2
(45) Date of Patent: Sep. 7, 2021

(54) METHOD FOR PERFORMING AN OPTICAL THREE-DIMENSIONAL RECORDING

(71) Applicant: SIRONA DENTAL SYSTEMS GMBH, Bensheim (DE)

(72) Inventors: Anders Adamson, Darmstadt (DE); Tom Bobach, Bensheim (DE); Nico Grund, Heppenheim (DE)

(73) Assignee: DENTSPLY SIRONA Inc., York, PA (US)

( * ) Notice: Subject to any disclaimer, the term of this patent is extended or adjusted under 35 U.S.C. 154(b) by 101 days.

(21) Appl. No.: 15/305,952

(22) PCT Filed: Apr. 23, 2015

(86) PCT No.: PCT/EP2015/058767
§ 371 (c)(1),
(2) Date: Oct. 21, 2016

(87) PCT Pub. No.: WO2015/162199
PCT Pub. Date: Oct. 29, 2015

(65) Prior Publication Data
US 2017/0056136 A1    Mar. 2, 2017

(30) Foreign Application Priority Data
Apr. 23, 2014    (DE) .................. 10 2014 207 667.6

(51) Int. Cl.
*A61C 9/00* (2006.01)
*A61B 1/00* (2006.01)
(Continued)

(52) U.S. Cl.
CPC ........ *A61C 9/0073* (2013.01); *A61B 1/00009* (2013.01); *A61B 1/00039* (2013.01);
(Continued)

(58) Field of Classification Search
CPC ... A61C 9/0073; A61C 9/0053; A61C 9/0046; A61C 9/0086; A61C 13/0004;
(Continued)

(56) References Cited

U.S. PATENT DOCUMENTS 4,837,732 A * 6/1989 Brandestini ............ A61C 9/006
433/29
5,372,502 A * 12/1994 Massen ............... A61C 13/0004
433/215
(Continued)

FOREIGN PATENT DOCUMENTS

JP    2008537494 A    9/2008
JP    2012066072 A    4/2012
(Continued)

OTHER PUBLICATIONS

International Search Report; PCT/EP2015/058767; Jul. 29, 2015 (completed); dated Aug. 2015.
(Continued)

*Primary Examiner* — Jacqueline T Johanas
*Assistant Examiner* — Shannel Nicole Belk
(74) *Attorney, Agent, or Firm* — DENTSPLY SIRONA Inc.

(57) ABSTRACT

The invention relates to a method for performing an optical three-dimensional recording by using hand-held dental camera. The camera automatically records a plurality of individual optical recordings in succession at a defined frequency during the measurement. The individual three-dimensional optical recordings are combined into an overall recording of a dental object to be measured and before the measurement is performed, a three-dimensional standard jaw model is displayed using a display device and a first control point on the standard jaw model is displayed using the display device. The hand-held dental camera is then (Continued)

positioned in relation to the object to be recorded in such a way that the camera points at the first control point of the standard jaw model and records a corresponding recording region of the dental object.

18 Claims, 3 Drawing Sheets

(51) Int. Cl.
    *A61B 1/045*     (2006.01)
    *A61B 1/24*     (2006.01)

(52) U.S. Cl.
    CPC ...... *A61B 1/00045* (2013.01); *A61B 1/00055* (2013.01); *A61B 1/045* (2013.01); *A61B 1/24* (2013.01); *A61C 9/0053* (2013.01)

(58) Field of Classification Search
    CPC . A61C 9/004; A61B 1/00009; A61B 1/00039; A61B 1/00045; A61B 1/00055; A61B 1/045; A61B 1/24
    USPC ............................................. 433/24, 29, 215
    See application file for complete search history.

(56) References Cited

U.S. PATENT DOCUMENTS

| | | | | |
|---|---|---|---|---|
| 9,336,336 | B2* | 5/2016 | Deichmann | A61C 13/0004 |
| 2001/0007138 | A1* | 7/2001 | Iida | G06F 11/0709 |
| | | | | 714/25 |
| 2006/0212260 | A1* | 9/2006 | Kopelman | A61B 5/1077 |
| | | | | 702/152 |
| 2006/0263739 | A1* | 11/2006 | Sporbert | A61C 7/00 |
| | | | | 433/24 |
| 2007/0207441 | A1* | 9/2007 | Lauren | A61C 13/0004 |
| | | | | 433/213 |
| 2009/0298017 | A1* | 12/2009 | Boerjes | A61C 13/0022 |
| | | | | 433/214 |
| 2010/0281370 | A1* | 11/2010 | Rohaly | A61C 9/0053 |
| | | | | 715/719 |
| 2011/0102549 | A1* | 5/2011 | Takahashi | A61C 1/084 |
| | | | | 348/46 |
| 2011/0105894 | A1* | 5/2011 | Kopelman | A61B 5/1077 |
| | | | | 600/425 |
| 2013/0286174 | A1 | 10/2013 | Urakabe | |
| 2013/0329020 | A1* | 12/2013 | Kriveshko | A61B 1/00009 |
| | | | | 348/50 |
| 2014/0365140 | A1* | 12/2014 | Popilka | A61C 19/04 |
| | | | | 702/19 |
| 2015/0206306 | A1* | 7/2015 | Adamson | A61C 9/0053 |
| | | | | 433/215 |
| 2015/0289756 | A1* | 10/2015 | Schmitt | A61C 9/004 |
| | | | | 704/235 |
| 2015/0296184 | A1* | 10/2015 | Lindenberg | A61C 9/0046 |
| | | | | 348/77 |
| 2017/0056136 | A1* | 3/2017 | Adamson | A61B 1/045 |

FOREIGN PATENT DOCUMENTS

| | | |
|---|---|---|
| JP | 2012157692 A | 8/2012 |
| WO | 2014027026 A1 | 2/2014 |

OTHER PUBLICATIONS

Written Opinion of the International Searching Authority; PCT/EP2015/058767; Jul. 29, 2015 (completed); dated Aug. 12, 2015.
International Preliminary Report on Patentability; PCT/EP2015/058767; Jul. 29, 2015 (completed); dated Aug. 12, 2015.

* cited by examiner

METHOD FOR PERFORMING AN OPTICAL THREE-DIMENSIONAL RECORDING

CROSS-REFERENCE TO RELATED APPLICATIONS

This is a National Phase application of International Application No. PCT/EP2015/058767 filed Apr. 23, 2014, which claims the benefit of and priority to German Application Ser. No. 102014207667.6, filed on Apr. 23, 2014, which are herein incorporated by reference for all purposes.

TECHNICAL FIELD

The invention relates to a method for performing an optical three-dimensional recording by using a hand-held dental camera, wherein the camera records a plurality of individual optical recordings in succession during the measurement. The individual three-dimensional optical recordings are then combined by means of registration into an overall three-dimensional recording of a dental subject to be measured.

BACKGROUND OF THE INVENTION

Multiple registration methods in which a plurality of individual optical recordings are performed and a subsequent registration ensues are known from prior art. During the registration, coincident areas—what are known as overlapping areas—are identified and registered together so that an overall recording is formed from the individual optical recordings.

This measurement, what is known as an on-the-fly measurement, can lead to an incorrect registration. This can, for example, be caused by overlapping areas being too small, by recording errors, or by interfering objects such as cheeks or tongues in the individual recordings.

One disadvantage of this method is that the hand-held dental camera is moved freely by the user without a user guidance during the manual measurement. This can, therefore, result in some areas of the subject being repeatedly measured unnecessarily, thereby increasing the data volume to be registered and the recording time. It is also possible for some areas of the subject to be left out during the measurement, leading to gaps being created. These gaps must then subsequently be filled by additional recording sequences.

The object of the present invention is therefore to provide a method that enables a reliable, complete and rapid measurement of the subject with a repeatable registration situation.

SUMMARY OF THE INVENTION

The invention relates to a method for performing an optical three-dimensional recording by using a hand-held dental camera, wherein the camera automatically records a plurality of individual optical recordings in succession at a set frequency during the measurement. The individual three-dimensional optical recordings are then combined by means of a registration method into an overall recording of a dental subject to be measured. Before the measurement is performed, a three-dimensional standard jaw model is displayed by means of a display device, wherein a first control point on the standard jaw model is displayed by means of the display device. The hand-held camera is then positioned in relation to the subject to be recorded in such a way that the camera points at the first control point of the standard jaw model and records a corresponding recording region of the dental subject in an optical recording.

The camera therefore automatically records a plurality of individual recordings during the measurement, for example at a frequency of 18 Hz, wherein the hand-held camera is moved relative to the subject. Therefore, the individual recordings do not need to be triggered manually.

The optical recordings are measured by means of the dental camera which, for example, can function according to a fringe projection method. In the fringe projection method, the individual fringes projected onto the subject are identified based on intensity, color, polarization, coherence, phase, contrast, location or duration. The 3D coordinates of the individual measuring points on the subject are then calculated using a triangulation method. The color encoding enables each of the color fringes to be unambiguously identified based on a specific order of the color fringes. For example, a slide or a grid can be used to generate a fringe pattern.

Alternatively, a confocal measurement method may also be used to record the individual three-dimensional recordings of the subject.

During the measurement, the hand-held dental camera is moved relative to the dental subject (such as a lower jaw or an upper jaw), wherein the three-dimensional optical images are generated at regular time intervals. The individual images can, for example, be generated at a clock frequency between 10 Hz and 20 Hz. The registration is performed by means of a computer which evaluates the recordings recorded. The ICP registration process (Iterative Closest Point algorithm) can be used as the registration method, for example. This algorithm is a known process for registering two-dimensional or three-dimensional subjects. The objective of this method is to align two different 3D models of a subject with one other at a minimal distance. To this end, different rotations and translations are applied to corresponding pairs of points of the two recordings to be registered, thereby minimizing a quadratic error of the distances between the pairs of points. This iterative convergence is performed until the two recordings coincide within the overlapping area.

As an alternative or in addition, the registration can also take place on the basis of the color of the recorded subject, the surface curvature of the recorded subject or on the basis of characteristic geometries of the subject. Given registration on the basis of characteristic geometries, a pattern recognition algorithm is used whereby the two recordings to be registered are searched for a specific geometric pattern, such as for an occlusal surface of a specific tooth.

The registration process can lead to registration errors if, for example, the camera moves too quickly in relation to the subject, resulting in the size of the overlapping area being insufficient. Another reason could be that the autofocus of the digital camera is not sharply set, thereby causing the subject to be indistinctly imaged such that the recording quality of the image is insufficient. An additional reason could be that movable objects such as the tongue of the patient or a finger of the treating dentist are recorded during measurement. Consequently, the overlapping areas of the images do not correspond.

Given this process, a user guidance takes place before the measurement is performed, wherein the first control point is displayed by means of a display device on the three-dimensional standard jaw model (which can be stored in a memory of a computer).

The display device can, for example, be a monitor that is connected to a computer. The standard jaw model can, for example, be displayed semi-transparently, wherein the individual recordings as well as the registered overall recording can be represented as an opaque three-dimensional model in superposition with the standard jaw model. The user can thereby visually identify in a simple manner which areas of the jaw have already been measured.

The dental subject can also be an individual tooth, a group of teeth, or a preparation for a tooth replacement part to be implanted.

Therefore, the first control point can thereby be arranged as user guidance in the area of the preparation in order to measure it completely.

The standard jaw model can thereby be modified conditional upon patient data. If, for example, specific teeth of the patient's jaw to be measured (such as the back molars with the FDI umbers 18, 28, 38 or 48) are missing, these teeth will also be missing from the standard jaw model. If it is known from the patient data that a specific tooth has been repaired, the standard jaw model can also have a standardized preparation. This enables the user to orient himself more easily within the tooth situation to be measured.

The first control point on the standard jaw model is therefore displayed for user guidance so that the user identifies in which area of the jaw he should begin with the measurement.

The control point can be emphasized in color or graphically, for example.

The control point can be represented in any number of ways, for example as a point, as a red circle or as a cross.

An advantage of this method is that the user guidance enables a repeatable measurement of the object and a reliable registration on the standard jaw model by means of the display device due to the fact that the subject can be measured in the same way following the control points along the displayed recording paths.

A further advantage of this method is that—in contrast to an on-the-fly measurement—the subject is not measured arbitrarily but rather along the optimized recording paths, so that recording time and data volumes are minimized.

A further advantage of this method is that a reliable global registration is made possible, as all clusters are registered relative to one another in a stable framework due to the optimized recording paths.

Advantageously, the correctness of the position of the first control point can be confirmed by a user action.

The user can thereby confirm the correctness of the position of the first control point without putting the camera down.

Advantageously, the user can hold the dental camera steady on the first control point, relative to the subject, for a defined period of time until an acoustic, visual and/or haptic signal ensues as feedback.

In this way, the dental camera can be held steady over the control point, for example for a duration of 2 seconds. An acoustic, visual and/or haptic signal can ensue as a feedback, for example by means of an LED on the camera, by vibration or by a beep tone. The user is thereby informed that the first control point has been confirmed.

The velocity or the acceleration of the camera relative to the subject can be determined using acceleration sensors in the camera, or also by evaluating the individual recordings. In so doing, the change in characteristic structures in the recordings is determined and the velocity is determined therefrom.

The signal as feedback can, for example, ensue if the acceleration or the velocity of the camera relative to the subject does not exceed a specific threshold value for a specified duration.

Advantageously, the user can confirm the first control point by actuating a button on the camera.

In so doing, the user can confirm the first control point without taking his hand from the camera.

Advantageously, the user can confirm the first control point by performing a gesture with the camera.

A gesture can, for example, be a single or double motion of the hand-held camera to the right. This is then interpreted as a command to confirm the first control point and to mark it accordingly in the software at the display device.

Advantageously, the user can confirm the first control point by means of a voice command in that the voice command is recorded in an audio recording and detected by means of voice recognition.

In this way the user can therefore confirm the control point by saying the respective voice command.

Advantageously, the user can confirm the first control point by operating an input means such as a mouse or a keyboard.

In this way the user can therefore confirm the control point by means of the input means which are connected to the computer.

Advantageously, the dental subject can be an entire upper jaw and/or a lower jaw.

The dental subject can therefore be the entire upper jaw, the entire lower jaw, or also an individual tooth, a group of teeth or a preparation.

Advantageously, the first control point for the measurement of an entire upper or lower jaw can be arranged in the middle of an occlusal surface of a molar which is located on a left end or on a right end of the standard jaw model.

As a result the first control point can, for example, be in the center of the occlusal surface of a molar 18 (top right), of a molar 28 (top right) for the top jaw, or of a molar 48 (bottom right), or of a molar 38 (bottom left) of a bottom jaw, in accordance with the FDI ordontogram. This control point is therefore already defined prior to the measurement on the standard jaw model.

Advantageously, the user can shift the position of the defined first control point relative to the standard jaw model using an input means, thereby redefining said position.

Therefore, the user can thereby shift the first control point by means of an input means (such as a mouse) and adjust it to the actual tooth situation. For example, in the event that the back molars 18, 28, 48 or 38 according to the FDI ordontogram are missing. An additional reason for the adjustment could be measurements of the actual jaw that deviate from the standard jaw model.

Advantageously, in addition to the first control point a second control point can be defined on an opposing end of the jaw to be measured and can be displayed by means of the display device, wherein a first recording path is defined between the first control point and the second control point, which path is displayed on the standard jaw model by means of the display device.

As a result, a recording path is defined between a first control point on the molar 18 or 48 and a second control point on the molar 28 or 38, which path is able to pass through the tooth centers of the individual teeth in the standard jaw model. The tooth centers are thereby defined as centers of the occlusal surfaces of the molars or as the middle of the incisal edges of the incisors. This recording path then corresponds to the optimum measurement movement of the camera for the occlusal measurement. The graphically displayed recording path serves as a user guidance for the user during the measurement.

Advantageously, an occlusal measurement can be performed from an occlusal direction relative to the jaw, wherein the manually held dental camera is moved along the displayed first recording path until the second control point is reached.

In this way the jaw is therefore measured from an occlusal direction.

Advantageously, the correctness of the position of the second control point can be confirmed by a user action.

In this way, the second control point can also be confirmed by one of the actions described above, such as holding the camera steady or by activating a button on the camera.

Advantageously, a lingual or a palatal measurement can be performed of tooth surfaces lying in an oral direction of the upper jaw or of the lower jaw as a subject. In so doing, a third control point is defined on the opposing end of the jaw originating from the second control point, wherein a second recording path is defined between the second control point and the third control point and displayed by means of the display device. The hand-held camera is then moved along the second recording path during the measurement, wherein the position of the third recording point is confirmed by a user action. The third control point can thereby have the same position as the first control point.

As a result, a lingual or palatal measurement of the upper jaw or of the lower jaw is performed along the second recording path as user guidance.

Advantageously, a buccal measurement can be performed from a buccal direction, wherein in a first step a first buccal measurement is performed originating from a fourth control point on a first end of the jaw arch to the middle of the jaw arch and furthermore to a fifth control point along a third recording path, wherein subsequently in a second step a second buccal measurement is performed originating from a sixth control point on a second opposing end of the jaw arch to the middle of the jaw arch and furthermore to a seventh control point along a fourth recording path, which is displayed by means of the display device.

As a result, a buccal measurement of the upper jaw or the lower jaw is performed along the third and the fourth recording path as user guidance.

Advantageously, a first cluster from the first buccal measurement and a second cluster from the second buccal measurement can be registered relative to one another using a shared overlapping area in the middle of the jaw arch.

In this way the two clusters are registered relative to the overall recording of the entire jaw arch.

Advantageously, at least one fringe recording sequence can be performed in a buccal direction, perpendicular to a jaw curve of the jaw arch to be measured along a fifth recording path which is displayed by means of the display device prior to the measurement of this fringe recording sequence. In so doing, the clusters previously generated from the occlusal measurement, the lingual measurement and/or the buccal measurement are linked to one another, thereby improving the registration.

Due to the measuring of the fringe recording sequence, the image data of the clusters from the occlusal measurement, the lingual measurement and/or the buccal measurement are linked to one another. To improve the registration, two or three fringe recording sequences can also be performed, for example top right, middle, top left for the upper jaw or bottom right, middle, bottom left for the lower jaw.

Advantageously, a bite block registration can be performed, wherein a first three-dimensional model of the upper jaw is registered relative to a second three-dimensional model of the lower jaw. In so doing, a buccal recording sequence is measured in a bite block position along a seventh recording path which is displayed between the corresponding control points by means of the display device.

In this way, therefore, a bite block registration is performed, wherein the seventh recording path (which is depicted by means of the display device) serves as a user guidance.

The jaw curves determined for the upper jaw and the lower jaw can also be used for the bite block registration in that the two jaw curves are aligned parallel to one another. The buccal recording sequence is then used to perform a finer registration of the upper jaw to the lower jaw.

Advantageously, an actual recording path of the camera can be determined which is formed by the projections of the centers of the individual recordings along a camera axis on a surface of the subject, wherein the actual recording path of the camera is displayed by means of the display device.

In so doing, a deviation between the actual recording path and the planned recording path can be determined during the measurement.

In the event that this deviation falls below a defined threshold value, an error message can be displayed by means of the display device. The user can then be asked to continue the measurement at a new control point.

The actual recording path of the camera can therefore be determined, wherein the centers of the recording areas of the recordings are graphically represented and connected. This allows the user to easily follow the deviation between the actual recording path, the camera and the planned first recording path.

To improve the registration, the determined jaw curve from the occlusal recording, which connects the actual tooth centers of the teeth, can be used for what is known as an outlier rejection.

Structures which are arranged outside a defined distance relative to the jaw curve, for example, can be hidden in the occlusal measurement.

Only structures up to the jaw curve are considered for the lingual measurement, and structures which are arranged in a buccal direction behind the jaw curve are hidden.

Only structures up to the jaw curve are considered for the buccal measurement, and structures which are arranged in a lingual direction behind the jaw curve are hidden.

In this way, therefore, interfering objects such as the tongue of the patient or finger of the treating dentist are hidden due to the fact that they are arranged further away from the jaw curve than the tooth substance of the teeth to be recorded.

Advantageously, the standard jaw model in superposition with the previously registered individual recordings can be pivoted, depending on a recording direction of the camera, in such a way that surfaces of the subject to be recorded are displayed, wherein the standard jaw model is displayed in the occlusal direction during the occlusal measurement, wherein during the lingual measurement the standard jaw model is pivoted such that the lingual surfaces to be recorded and the previously recorded occlusal surfaces of the teeth are visible, wherein during the buccal measurement the standard jaw model is pivoted such that the buccal surfaces to be recorded and the previously recorded occlusal surfaces of the teeth are visible.

In this way, the user can better orient himself on the standard jaw model during the measurement. This is due to the fact that the surfaces to be recorded are clearly displayed.

Advantageously, with the aid of a computer it is possible to automatically determine in which areas the registered overall recording of the subject has gaps, wherein additional control points and/or additional recording paths are displayed in succession in these areas on the standard jaw model for user guidance.

As a result, the automatic user guidance takes place control point for control point for as long as it takes for all gaps to be filled and the overall recording to be complete without gaps.

Advantageously, specific areas of the subject which are to be completely measured and which contain a preparation, for example, can be defined on the standard jaw model before the measurement, wherein it is checked with the aid of a computer whether these areas have been completely measured or whether they have gaps, wherein—in the event that these areas have gaps—additional control points and/or additional recording paths are displayed on the standard jaw model in order to measure these areas completely.

In this way it is ensured that significant areas of the subject are measured completely and without gaps, for example for the planning of tooth replacement parts.

BRIEF DESCRIPTION OF THE DRAWINGS

The invention is explained with reference to the drawings. The figures depict the following.

DETAILED DESCRIPTION OF THE INVENTION

Figure 1:
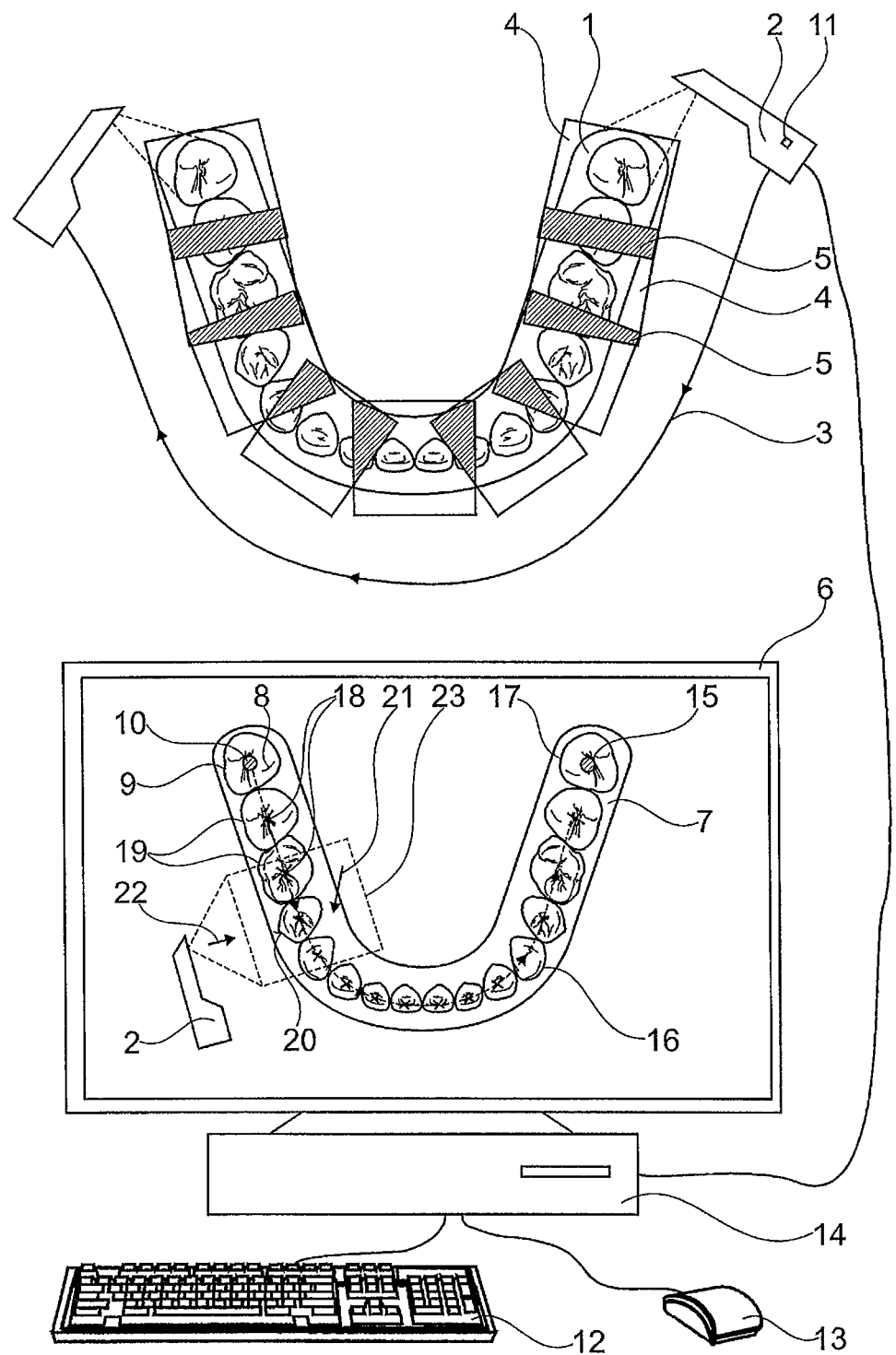
FIG. 1 a sketch to illustrate the present method for performing an optical three-dimensional recording.

FIG. 1 depicts a sketch to illustrate the present invention of an optical three-dimensional recording of a dental subject 1 to be measured, such as a bottom jaw, by means of a hand-held dental camera 2 which is pivoted around the dental subject 1 along a trajectory 3. The three-dimensional optical recordings 4, which are represented in the form of rectangles, are measured by means of the dental camera 2 which is pivoted along the trajectory 3 around the subject 1 during the measurement. The camera 2 is a hand-held camera which works using a fringe projection method. The recordings 4 are registered relative to one another using the overlapping areas 5 which are shown as dashed lines, thereby generating an overall recording of the object 1. Prior to the measurement being performed, a three-dimensional standard jaw model 7 is displayed by means of a display device 6 such as a monitor, which model corresponds in its measurements to an average jaw arch. In so doing, a first control point 10 is displayed on the standard jaw model of the lower jaw, bottom right, on the left end of the standard jaw model 7 in the middle of an occlusal surface 8 of the back molar 9 with the FDI number 38, bottom left. The control point 10 is represented schematically as a black circle. The user then moves the dental camera in the area of the molar 9 so that the camera records the first control point 10. The camera 2 is then held steady over the first control point for a defined period of time until an acoustic, visual and/or haptic signal ensues as a feedback and the position of the first control point is thereby confirmed. The first control point 10 can also be confirmed by operating a button 11 on the camera 2.

Alternatively, the control point 10 can also be confirmed by means of the input means, such as a keyboard 12 and a mouse 13, which are connected to a computer 14.

A second control point 15 and a first recording path 16 are displayed in addition to the first control point. The second control point is thereby arranged on the opposing end of the jaw arch on the back molar 17 with the FDI number 48. The recording path 16 thereby runs through the tooth centers 18 of the individual teeth 19 of the standard jaw model 7. The displayed recording path serves as a user guidance for the user in order to display which areas of subject 1 are to be measured.

For orientation, the standard jaw model 7 can be pivoted such that buccal surfaces 20 of a recording area 23 (which is shown as a dashed line) that are to be recorded are displayed in the foreground, wherein the previously measured occlusal surfaces of the subjects are also visible.

In this way, the line of sight on the standard jaw model 7 is changed during the measurement simultaneous with the movement of the camera 2 so that the user, such as the dentist, can orient himself more easily within the tooth situation.

Figure 2:
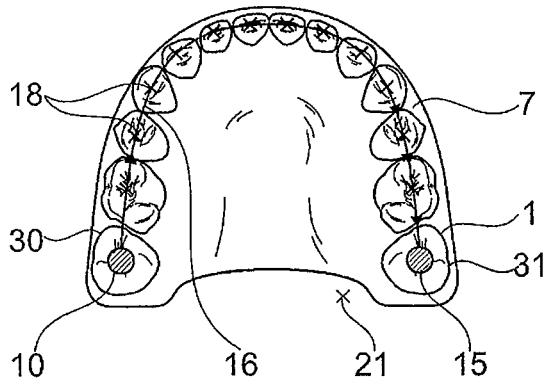
FIG. 2 a sketch of a standard jaw model of an upper jaw for an occlusal measurement.

FIG. 2 depicts a sketch of a standard jaw model 7 of an upper jaw, wherein the first recording path 16 originating from a first control point 10 (top right) on a first molar 30 with the FDI number 37 runs up to the second control point 15 on the opposing end of the jaw arch on the second molar 31 with the FDI number 47. The recording path 16 thereby runs through the tooth centers 18 of the individual teeth 19 of the standard jaw model 7. The dental camera 2 is therefore moved such that a center of the recordings 4 coincides with the recording path 16. In this way, an occlusal measurement is therefore carried out from the occlusal direction 21 of the top jaw.

Figure 3:
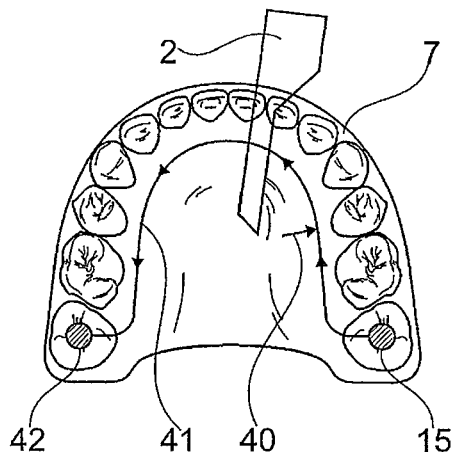
FIG. 3 a sketch of a standard jaw model of an upper jaw for a lingual measurement.

FIG. 3 depicts a sketch to illustrate a lingual measurement of the upper jaw from a lingual or oral direction 40, which is represented by an arrow. The camera 2 is then positioned relative to the subject 1 in such a way that the recording from this direction 40 is facilitated, as indicated in FIG. 3. The lingual measurement is carried out along a second recording path 41 originating from the second control point 15 toward a third control point 42. Therefore, the inside tooth surfaces of the upper jaw are measured with the lingual measurement.

Figure 4:
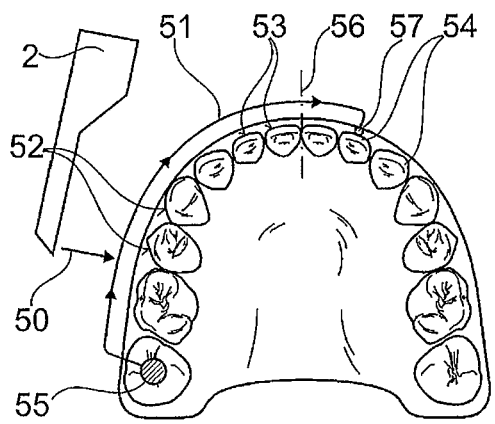
FIG. 4 a sketch of a standard jaw model of an upper jaw for a first step of a buccal measurement.

FIG. 4 depicts a sketch to illustrate a buccal measurement from a buccal direction 50, wherein a camera 2 is pivoted around the jaw in such a way that the buccal tooth surfaces 52 and the labial tooth surfaces 53 are measured. The teeth 54 are therefore not measured in the first step. The third recording path 51 thereby runs originating from a fourth control point 55 at the molar with the FDI number 37 across a middle 56 of the jaw arch up to a fifth control point 57. The position of the fourth control point 55 can thereby correspond to the position of the control point 42 and the control point 10.

Figure 5:
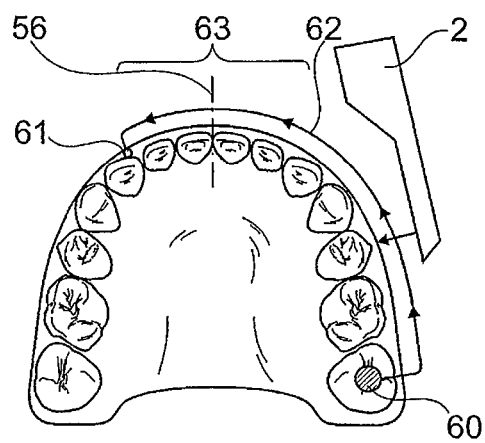
FIG. 5 a sketch of a standard jaw model of an upper jaw for a second step of a buccal measurement.

FIG. 5 depicts a second buccal measurement originating from a sixth control point 60 across the middle 56 of the jaw arch to a seventh control point 61 along a fourth recording path 62. A first cluster from the first buccal measurement from FIG. 4 and a second cluster from the second buccal measurement from FIG. 5 are then registered relative to one another using a shared overlapping area 63 in the middle of the jaw arch.

Figure 6:
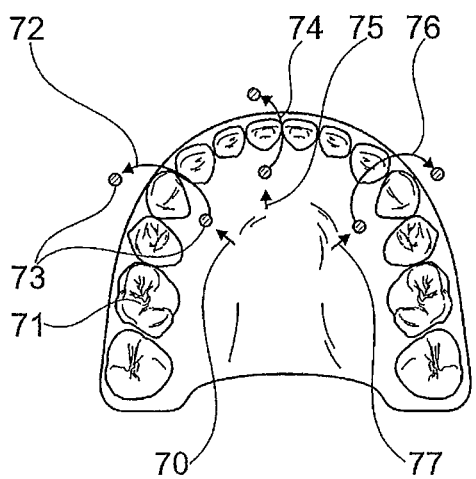
FIG. 6 a sketch to illustrate a plurality of fringe recording sequences.

FIG. 6 depicts a sketch to illustrate a first fringe recording sequence in buccal direction 70 perpendicular to a jaw curve 71 of the jaw arch to be measured along a fifth recording path 72 between the control points 73. The fifth recording path 72 thereby runs in the area of a molar with the FDI number 14. In addition, a second fringe recording sequence is performed in the labial direction 75 along a sixth recording path 74 in the area of the incisor with the FDI number 11, and a third fringe recording sequence is performed in the buccal direction 77 along the seventh recording path 76 in the area of the molar with the FDI number 24.

Figure 7:
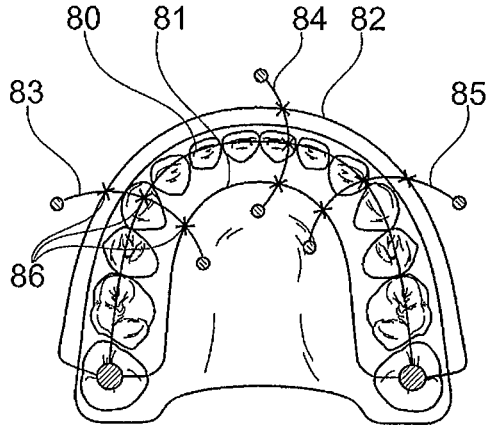
FIG. 7 a sketch to illustrate a linking of the different clusters.

FIG. 7 depicts a sketch which is to illustrate that a first cluster 80 from the occlusal measurement in FIG. 2, a second cluster 81 from the lingual measurement in FIG. 3 and a third cluster 82 from the buccal direction in FIG. 4 and FIG. 5 are linked to each other by the fourth cluster 83 of the first fringe recording sequence from FIG. 6, as well as by the fifth cluster 84 of the second fringe recording sequence and the sixth cluster 85 of the third fringe recording sequence. The linkage points 86 are indicated by the crosses.

Figure 8:
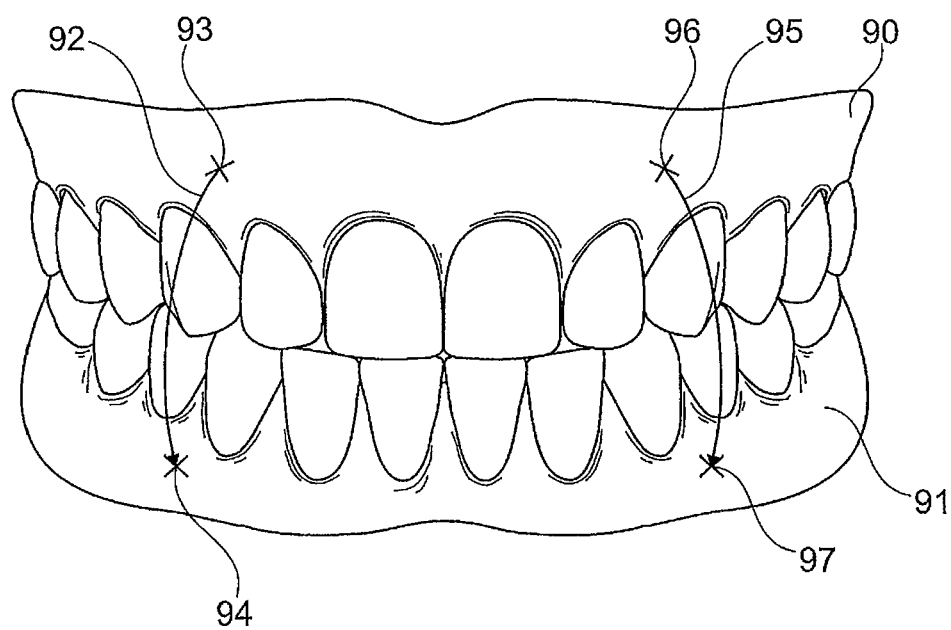
FIG. 8 a sketch to illustrate a bite block registration.

FIG. 8 depicts a sketch to illustrate a bite block registration, wherein a first three-dimensional model 90 of the upper jaw is registered relative to a second three-dimensional model 91 of the lower jaw. In this way, a first buccal recording sequence is performed along a recording path 92 between the control points 93 and 94, and a second buccal recording sequence is performed along the recording path 95 between a control point 96 and a control point 97. The first buccal recording sequence thereby runs in the area of the teeth with the FDI numbers 14 and 44. The second buccal recording sequence runs in the area of the teeth with the FDI numbers 24 and 34.

REFERENCE CHARACTERS

1 Subject
2 Camera
3 Trajectory
4 Recording
5 Overlapping area
6 Display device
7 Standard jaw model
8 Occlusal surface
9 Molar
10 Control point
11 Button
12 Keyboard
13 Mouse
14 Computer
15 Second control point
16 First recording path
17 Back molar
18 Tooth centers
19 Teeth
20 Buccal surfaces
21 Occlusal direction
22 Buccal direction
23 Recording area
30 First molar
31 Second molar
40 Direction
41 Recording path
50 Buccal direction
51 Third recording path
52 Buccal tooth surface
53 Labial tooth surface
54 Teeth
55 Fourth control point
56 Middle
57 Fifth control point
60 Sixth control point
61 Seventh control point
62 Third recording path
63 Overlapping area
70 Direction
71 Jaw curve
72 Fifth recording path
73 Control point
74 Sixth recording path
75 Seventh recording path
76 Direction
80 First cluster
81 Second cluster
82 Third cluster
83 Fourth cluster
84 Fifth cluster
85 Sixth cluster
86 Linkage point
90 First three-dimensional model
91 Second three-dimensional model
92 Recording path
93 Control point
94 Control point
95 Recording path
96 Control point
97 Control point

The invention claimed is:

1. A method of recording three-dimensional images of a physical jaw using a dental camera, comprising:
displaying a virtual three-dimensional standard jaw model corresponding to the physical jaw on a display device;
displaying a first and a second virtual control point on a first and second virtual tooth of the virtual three-dimensional standard jaw model respectively;
determining a virtual recording path disposed between two virtual teeth, said virtual recording path disposed between two virtual teeth is defined by a visible path disposed between the first virtual control point on the first virtual tooth and the second virtual control point on the second virtual tooth, the first virtual tooth is different from the second virtual tooth;
displaying said virtual recording path disposed between two virtual teeth on the virtual three-dimensional standard jaw model;
operating the camera to automatically generate a plurality of three-dimensional images of the physical jaw in succession along portions of the physical jaw corresponding to the virtual recording path, by moving the dental camera relative to the physical jaw and automatically recording the plurality of three-dimensional images at a constant frequency, the automatic recording at the constant frequency starts from a portion of the physical jaw corresponding to the first virtual tooth, follows a direction of the virtual recording path, and ends at another portion of the physical jaw corresponding to the second virtual tooth.

2. The method according to claim 1, wherein the dental camera is positioned over an area of a full upper jaw and/or a lower jaw.

3. The method according to claim 1, further comprising acquiring at least one of occlusal, lingual or palatal and buccal measurements by acquiring a plurality of individual optical recordings in an occlusal, lingual or palatal and buccal parts of physical jaw and registering the plurality of individual optical recordings into an overall three-dimensional recording using a registration process.

4. The method according to claim 1, wherein the virtual recording path disposed between two virtual teeth runs through tooth centers of individual virtual teeth of the virtual three-dimensional standard jaw model.

5. The method according to claim 1, further comprising confirming a position of the first and/or second virtual control points displayed on the virtual three-dimensional standard jaw model by (i) actuating a button on the dental camera, (ii) performing a gesture with the dental camera, (iii) providing a voice command, and/or (iv) providing a command through an input device.

6. The method according to claim 1, wherein the first and second virtual control points are determined on the first and second virtual teeth respectively in an occlusal area of the virtual three-dimensional standard jaw model, and the virtual recording path disposed between two virtual teeth is disposed between the first and second virtual control points in the occlusal area, such that the occlusal measurement is performed on the physical jaw in an occlusal direction of the physical jaw in a manner that follows the direction of the virtual recording path disposed between two virtual teeth.

7. The method according to claim 1, wherein the first and second virtual control points are determined on the first and second virtual teeth respectively in a lingual or palatal area of the virtual three-dimensional standard jaw model, and the virtual recording path disposed between two virtual teeth is disposed between the first and second virtual control points in the lingual or palatal area, such that the lingual or palatal measurement is performed on the physical jaw in a lingual or palatal direction of the physical jaw in a manner that follows the direction of the virtual recording path disposed between two virtual teeth.

8. The method according to claim 1, wherein the first and second virtual control points are determined on the first and second virtual teeth respectively in a buccal area of the virtual three-dimensional standard jaw model, and the virtual recording path disposed between two virtual teeth is disposed between the first and the second virtual control points in the buccal area, such that the buccal measurement is performed on the physical jaw in a buccal direction of the physical jaw in a manner that follows the direction of the virtual recording path disposed between two virtual teeth.

9. The method according to claim 8, wherein another first and another second virtual control points are determined on another first and second virtual teeth respectively in another buccal area of the virtual three-dimensional standard jaw model, and another virtual recording path disposed between another two virtual teeth is disposed between the first and the another second virtual control points in the another buccal area, such that another buccal measurement is performed on the physical jaw in another buccal direction of the physical jaw, in a manner that follows the direction of the virtual recording path disposed between two virtual teeth and wherein the buccal measurement and the another buccal measurement are registered together using a shared overlapping area.

10. The method according to claim 1, wherein the first and second virtual control points are determined on the first and second teeth respectively in a further buccal or labial area of the virtual three-dimensional standard jaw model, and the virtual recording path disposed between two virtual teeth is disposed between the first and the second virtual control points in the further buccal or labial area, such that a further buccal or labial measurement is performed on the physical jaw in a further buccal or labial direction perpendicular to a jaw curve of a jaw arch and wherein the recording includes at least one fringe recording sequence that includes fringe projections.

11. The method according to claim 1, wherein the first virtual control point is located on a first virtual three-dimensional model of an upper jaw and the second virtual control point is located on a second virtual three-dimensional model of a lower jaw and the virtual recording path disposed between two virtual teeth is determined such that the first virtual three-dimensional model of the upper jaw is registered with the second three-dimensional model of the lower jaw by performing a buccal measurement along the recording path when the upper jaw and lower jaw are in a bite position.

12. The methods according to claim 1 further comprising determining an actual recording path of the dental camera by connecting centers of the individual optical recordings.

13. The method according to claim 12, further comprising determining a deviation between the actual recording path of the dental camera and the virtual recording path disposed between two virtual teeth and (i) displaying an error message when the deviation exceeds a predetermined threshold and/or (ii) determining a new control point for a new recording path.

14. The method according to claim 1, further comprising determining one or more virtual gaps in the overall three-dimensional recording and determining additional virtual control points and/or additional virtual recording paths disposed between two virtual teeth for measuring regions in the physical jaw corresponding to the gaps.

15. The method according to claim 1, further comprising arranging the first virtual control point in a middle of an occlusal surface of a molar.

16. The method of claim 1, wherein a correctness of a position of the first control point and/or second control point is confirmed by user action.

17. A method of recording three-dimensional images of a physical jaw using a dental camera, comprising:
  displaying a virtual three-dimensional standard jaw model on a display device;
  displaying a plurality of first and second virtual control points on a plurality of first and second virtual teeth of the virtual three-dimensional standard jaw model respectively;
  determining a plurality of virtual recording paths each disposed between two virtual teeth said plurality of virtual recording paths each disposed between two virtual teeth are defined by a plurality of visible paths with each visible path of the plurality of visible paths disposed between one of the plurality of first virtual control points on one of the plurality of first virtual teeth and one of the plurality of second virtual control points on one of the plurality of second virtual teeth;
  displaying said plurality of virtual recording paths each disposed between two virtual teeth on the three-dimensional standard jaw model;
  sequentially operating the camera to automatically generate a plurality of three-dimensional images of the physical jaw in succession along portions of the physical jaw corresponding to the plurality of virtual recording paths, by moving the dental camera, for each virtual recording path of the plurality of virtual recording paths, relative to the physical jaw and automatically recording the plurality of three-dimensional images, for each virtual recording path, at a constant frequency, the automatic recording at the constant frequency starts from a portion of the physical jaw corresponding to a first virtual tooth, follows a direction of the virtual recording path, and ends at another portion of the physical jaw corresponding to a second virtual tooth.

18. The method according to claim 17 further comprising acquiring at least two clusters of occlusal, lingual or palatal and buccal measurements and registering at least two clusters of the occlusal, lingual or palatal, and buccal measurements together.

* * * * *